United States Patent [19]

Matsui et al.

[11] 4,447,605

[45] May 8, 1984

[54] DI(TRI-LOWER ALKYLSTANNYL)PYRIMIDINE DERIVATIVE AND A PROCESS FOR PRODUCING THE SAME

[75] Inventors: Masanao Matsui, Tokyo; Tomoya Ogawa, Musashino, both of Japan

[73] Assignee: Rikagaku Kenkyusho, Wako, Japan

[21] Appl. No.: 287,642

[22] Filed: Jul. 28, 1981

Related U.S. Application Data

[62] Division of Ser. No. 735,777, Oct. 28, 1976, Pat. No. 4,324,895.

[30] Foreign Application Priority Data

| Oct. 24, 1975 | [JP] | Japan | 50-128020 |
| Oct. 24, 1975 | [JP] | Japan | 50-128022 |
| Dec. 4, 1975 | [JP] | Japan | 50-144637 |
| Jan. 5, 1976 | [JP] | Japan | 51-180 |
| Mar. 15, 1976 | [JP] | Japan | 51-27836 |
| Mar. 15, 1976 | [JP] | Japan | 51-27837 |
| May 11, 1976 | [JP] | Japan | 51-53463 |

[51] Int. Cl.$^3$ .................................................. C07D 239/52
[52] U.S. Cl. .................................................... 544/225
[58] Field of Search ...................................... 544/225

[56] References Cited

U.S. PATENT DOCUMENTS

| 3,284,296 | 11/1966 | Freiberg | 424/245 |
| 3,419,662 | 12/1968 | Weissenberger | 424/245 |
| 3,446,827 | 5/1969 | Schwartz | 424/245 |
| 3,629,264 | 12/1971 | Pande | 424/245 |
| 3,912,734 | 10/1975 | Giller et al. | 544/313 |
| 3,960,864 | 6/1976 | Townsend et al. | 544/313 |

FOREIGN PATENT DOCUMENTS 51-23512 7/1976 Japan.

*Primary Examiner*—Paul M. Coughlan, Jr.
*Attorney, Agent, or Firm*—Fleit, Jacobson, Cohn & Price

[57] ABSTRACT

The present invention relates to a novel process for producing pyrimidine nucleosides by a reaction between bis(tri-lower alkylstannyl)-5-halogenouracil and 2-substituted tetrahydrofurane. The novel process of the present invention makes it possible to obtain, depending upon the manner of substitution of tetrahydrofurane residue on two nitrogen atoms $N_1$ and $N_3$ of 5-halogenouracil, $N_1$-mono-substituted compound, $N_3$-mono-substituted compound and $N_1$,N-di-substituted compound among which the last can be converted by hydrolysis thereof into $N_1$-mono-substituted compound. The present invention further relates to novel $N_3$-mono-substituted compounds and $N_1$,$N_3$-di-substituted compounds obtained by such process. The present invention still further relates to novel bis-(tri-lower alkylstannyl)-5-halogenouracil used in the present invention as a raw compound.

2 Claims, No Drawings

DI(TRI-LOWER ALKYLSTANNYL)PYRIMIDINE DERIVATIVE AND A PROCESS FOR PRODUCING THE SAME

This is a divisional of application Ser. No. 735,777, filed Oct. 28, 1976, now U.S. Pat. No. 4,324,895, which issued on Apr. 13, 1982.

FIELD OF THE INVENTION

The present invention relates to novel pyrimidine nucleosides or 5-halogenouracil substituted on the nitrogen atoms thereof with a 2'-tetrahydrofuranyl radical and a process for producing the same.

In recent years pyrimidine nucleosides have drawn attention as pharmaceuticals having diversified pharmaceutical effects, for example as an anticancer medicine with excellent therapeutic effect on various types of cancers.

Also pyrimidine nucleosides have become known as an antimetabolic agent in the fields of pharmaceuticals and agricultural chemicals and as a condiment in the food industries.

Amont the above-mentioned anticancer medicines most salient as 1-(tetrahydro-2-furanyl)-5-fluorouracil which is commonly known under the name of Ftorafur.

Ftorafur is a derivative of 5-fluorouracil (5-FU) which is bonded, at the N-1 position thereof, with 2-position of tetrahydrofurane residue, and functions as a masked compound which is gradually converted into an active compound such as 5-FU in the blood vessels and internal organs.

In clinical studies with injective administration Ftorafur proved to be similarly effective as 5-FU against cancers of the stomach, colon, rectum and other parts of the digestive tract, lung cancer and particularly gland cancers. The total dose required for positive result is 20–40 grams in total with a daily dose of 800–1,200 mgs.

Ftorafur in general shows significantly lighter secondary effects than in 5-FU, and causes almost no diarrhoea, perforation, medullary disorders or other serious secondary trubles which frequently occur in the administration of 5-FU. From this standpoint Ftorafur proved to be clinically far superior to 5-FU.

Also in oral administration, the antitumor effect of Ftorafur is particularly marked in breast cancer, and is comparable, in case of cancers of the digestive tract such as stomach cancer, to the effect of 5-FU obtained by intravenous administration. Also in this case, Ftorafur is far superior to 5-FU with respect to the secondary effects.

DESCRIPTION OF THE PRIOR ART

Pyrimidine nucleosides are already known to be synthesizable by means of so-called silicon process or mercury process, most prior reference being devoted to the former process.

In said silicon process, pyrimidine nucleosides are obtained by reacting bistrimethylsilyl derivative of uracil with acylated sugars or furane derivatives in the presence of Friedel-Crafts catalyst.

For example U. Nieballa and Helmut Vorgriggen (Angewandte Chemie 82, No. 11, 449–450) reported the synthesis of N1-nucleoside of uracil by reacting bis-trimethylsilyl derivative of uracil with 1-O-acetyl-2,3,5-tri-O-benzoyl-D-riboflanose in the presence of a Friedel-Crafts catalyst.

Also the Japanese Patent Publication 8551/1965 published on May 4, 1965 discloses a process for producing pyrimidine nucleosides represented by a general formula:

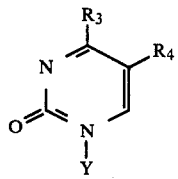

wherein $R_3$ and $R_4$ are members selected from hydrogen atom, hydroxyl radical, amino radical, mercapto radical and methyl radical and Y is a glucosyl radical; which comprises reacting a pyrimidine derivative represented by a general formula:

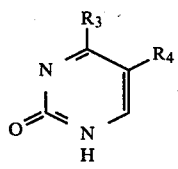

wherein $R_3$ and $R_4$ have the same meaning as explained above, with a tri-(lower alkyl)-chlorosilane or hexa-(lower alkyl)-disilazane in the presence of a tertinary amine and reacting thus obtained reaction product with a halogeno-pentose or a halogeno-hexose.

Furthermore the British Pat. No. 1,168,391 published Oct. 22, 1969 discloses a process for producing $N_1$-(2'-furanizyl)uracil or $N_1$-(2'-pyranizyl)uracil by reacting a bistrimethylsilyl derivative of uracil with 2-chlorofuranizine or 2-chlorophyranizine.

Said mercury process consists of a reaction between monomethylated pyrimidine and a 2-substituted tetrahydrofurane at a low temperature as reported in Doklady Akademii Nauk SSSR 176, No. 2, 332–335(1967) of which English translation was published in DOK-LADY CHEMISTRY 176, No. 1–3, 798–801 September (1967).

The synthesis of Ftorafur which is $N_1$-(2'-tetrahydrofuranyl)-5-fluorouracil, and the related compounds thereof by said silicon process or mercury process is already known in the various patents and patent applications which are enumerated here: Giller, U.S. Pat. No. 3,635,946; Giller U.S. Pat. No. 3,912,734; La Roche, U.S. Pat. No. 2,802,005; La Roche, U.S. Pat. No. 3,354,160; Knuniants, U.S. Pat. No. 3,682,917; Giller, U.S. Pat. No. 3,846,429; Taiho, Japanese Patent Publication 64281/1975; Taiho, Japanese Patent Publication 50383/1975; Taiho, Japanese Patent Publication 50384/1975; Taiho, Japanese Patent Publication 105673/1975; Taiho, Japanese Patent Publication 105,674/1975; Asahi, Japanese Patent Publication 127,981/1974; Asahi, Japanese Patent Publication 127,982/1974; and Asahi, Japanese Patent Publication 127,983/1974.

SUMMARY OF THE INVENTION

As explained in the foregoing, the pyrimidine nucleosides, particularly $N_1$-(2'-tetrahydrofuryl)-5-fluorouracil known under a name of FT-207 "Fotrafur" and the related compounds thereof, are known to be synthesizable either by said silicon process or by mercury process. However, said mercury process is disadvantageous in the use of a low-temperature reaction to be effected as low as −40° C. and also in the use of toxic mercury salts.

On the other hand said silicon process, though investigated by various investigators as mentioned before, is still associated with drawbacks, namely, that the side product resulting from trialkylsilicon is not recoverable and that pyrimidine trimethylsilylated in the course of reaction are difficult to handle due to the low stability thereof in the air. An another drawback in this process is that the trimethylsilylation is more difficult to realize in comparison with trialkylstannylation.

The present invention is based on a tin process utilizing a reaction between a stannylated pyrimidine derivative and a tetrahydrofurane derivative which, avoiding the above-mentioned drawbacks, makes it possible to obtain the desired compound with an elevated yield and at a nearly ambient temperature, and further makes it possible to obtain novel compounds which have not been reported in the prior references.

The object of the present invention, therefore, is to provide a process for producing pyrimidine nucleosides by means of such tin process.

An another object of the present invention is to provide a novel process for producing pyrimidine nucleosides wherein 5-halogenouracil is substituted, on a carbon atom thereof, with a tetrahydrofurane residue, by means of said tin process.

Still another object of the present invention is to provide a process for producing $N_1$-(2'-tetrahydrofuryl)-5-fluorouracil by means of said tin process.

Still another object of the present invention is to provide novel pyrimidine nucleosides obtained in connection with the development of said tin process.

Still further object of the present invention is to provide novel bis(tri-lower alkylstannyl)-5-halogenouracil.

Still another object of this invention is to provide a process for producing the said stannyl uracil derivatives.

Still other objects of the present invention will be clear from the following description of the present invention.

DESCRIPTION OF THE PREFERRED EMBODIMENTS

The present invention is to provide a process for producing pyrimidine nucleosides wherein a tetrahydrofurane reside is bonded to nitrogen atoms of pyrimidine nucleus by reacting a bis(tri-n-lower alkylstannyl)-5-halogenouracil with a 2-substituted tetrahydrofurane, also to provide pyrimidine nucleosides obtained by such process.

The bis(tri-n-lower alkylstannyl)-5-halogenouracil which is utilized as a starting material is a novel substance obtained by a reaction between 5-halogenouracil and bis(tri-n-lower alkylstannyl)oxide in a manner as explained in the following.

5-halogenouracil is heated under reflux with equimolar or approximately equimolar amount of bis(tri-lower alkylstannyl)oxide in the presence of an aprotic solvent such as toluene with continuous elimination of water. After the distillation of water is terminated, the solvent is distilled off to obtain crude bis(tri-n-lower alkylstannyl)-5-halogenouracil.

The reaction thus formed, due to the susceptibility thereof to atmospheric moisture is immediately subjected, without isolation or intermediate purification and with or without solvent substitution, to the succeeding reaction.

The foregoing reaction can be represented by the following reaction formula:

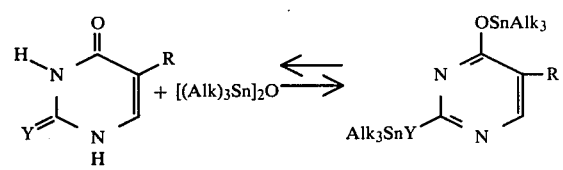

wherein R represents a halogen atom selected from fluorine, chlorine or bromine, Alk represents a lower alkyl radical and Y hydrogen, or a lower alkyl radical represents oxygen or sulfur atom. This reaction can be carried out in a solvent immiscible with water and having a suitable boiling point, as represented by aprotic solvents such as benzene or toluene. As this reaction is reversible reaction, it can be advanced to the right-hand side by eliminating water from the system.

Thus, in the above-mentioned reaction of 2,5-disubstituted pyrimidine derivative with bis(tri-lower alkylstannyl)oxide, the novel compound constituting the object of the present invention can be obtained quantitatively by refluxing the reaction mixture in an aprotic solvent such as benzene, carbon tetrachloride or toluene while eliminating water formed during the reaction.

The compounds thus obtained in this reaction can be easily hydrolized with water or ethanol into the original 2,5-disubstituted pyrimidine derivative.

The lower alkyl radical in the above reaction formula is not subjected to limitation as the alkylstannyl radical is cleaved by the following condensation reaction and does not contribute to the reaction. It is therefore possible to employ a bis(tri-lower alkylstannyl)oxide provided with a lower alkyl radical easily available and manipulatable.

The compounds are novel substances which can be utilized as important intermediates for the syntheses of various nucleosides for which excellent physiological activities are expected. For example β-nucleosides having excellent physiological activities (for example anticancer effect) can be obtained by reacting the object compounds of the present invention with completely acylated sugars.

As examples of said lower alkyl radical represented by Alk in the above-mentioned general formula can be mentioned methyl, ethyl, n-propyl, isopropyl, n-butyl, isobutyl, tert-butyl, n-pentyl, isopentyl and hexyl radicals, and the halogen atom represented by R can be exemplified by a fluorine, chlorine or bromine atom. Also the lower alkyl radicals represented by R can be any of the above-mentioned lower alkyl radicals and can be same as or different.

The followings are examples of the compound of the general formula (I): 2,4-bis(tri-n-butylstannyl)-5-fluorouracil; 2,4-bis(tri-n-butylstannyl)uracil; 2,4-bis(tri-isobutylstannyl)-5-methyluracil; 2,4-bis(tri-n-propylstannyl)-5-bromouracil; 2-thio(tri-n-butylstannyl)-4-tri-n-butylstannyluracil; 2,4-bis(triethylstannyl)-5-bromouracil; 2-thio(tri-n-pentylstannyl)-4-(tri-n-propylstannyl)uracil; 2,4-bis(trimethylstannyl)-5-butyluracil; and 2,4-bis(triethylstannyl)uracil.

According to the present invention the desired compound can be prepared by reacting bis(tri-lower alkylstannyl)-5-halogenouracil obtained as explained above with a 2-substituted tetrahydrofurane represented by the following general formula:

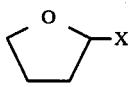

wherein X is a halogen atom, a lower alkyloxy or aralkyloxy radical, a lower alkylcarbonyloxy radical or an arylcarbonyloxy radical. Said halogen can for example be chlorine, bromine, fluorine or iodine; said lower alkyloxy radical can be methoxy, ethoxy, propoxy, isopropoxy, butoxy, isobutoxy or pentoxy; said lower alkylcarbonyloxy radical can be acetoxy, propionyloxy, butanoyloxy, pentaoyloxy, or hexaoyloxy; and said arylcarbonyloxy radical can be benxoxy, paramethylbenzoxy or parabromobenzoxy and aralkyoxy radical can be benzyloxy or phenylethyloxy.

The preferred examples of said 2-substituted tetrahydrofurane are 2-acetoxytetrahydrofurane, 2-chlorotetrahydrofurane, 2-methoxytetrahydrofurane, 2-benzoxytetrahydrofurane, 2-(p-nitrobenzoxy)tetrahydrofurane and 2-(p-tolylbenzoxy)tetrahydrofurane.

The above-mentioned reaction can be conducted within a temperature range of from about $-50°$ C. to about $100°$ C. and for a period of about 30 minutes to about 20 hours, and is characterized by the fact that the reaction product varies dependent on the molar ratio of reactants, reaction temperature and reaction period.

More specifically, said reaction provides $N_1$-bis(2'-tetrahydrofuranyl)-5-halogenouracil (hereinafter called compound I), $N_3$-bis(2'-tetrahydrofuranyl)-5-halogenouracil (hereinafter called compound II), N,N'-bis(2'-tetrahydrofuranyl)-5-halogenouracil (hereinafter called compound III) or a mixture of I and II, depending upon the reaction conditions. Said compounds are shown in the following:

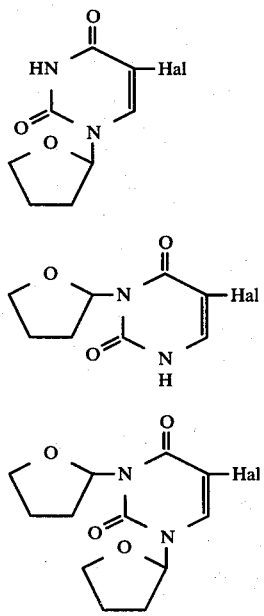

Compound I

Compound II

Compound III

Said reaction between bis(tri-lower alkylstannyl)-5-halogenouracil and said 2-substituted tetrahydrofurane is preferably conducted in a solution in a chlorinated hydrocarbon such as dichloromethane and if necessary in the presence of Friedel-Crafts catalyst. Preferred examples of such Friedel-Crafts catalysts are stannic chloride, $BF_3$ etherate, $AlCl_3$, $PCl_3$ and $ZnCl_2$. Such catalyst is not required in case the radical X in said 2-substituted tetrahydrofurane is a halogen atom, but otherwise the reaction can be made to proceed advantageously in the presence of a Lewis acid in a calculated or excessive amount.

Other examples of solvents employable in said reaction are dichloroethane, tetrachlorethane, trichloroethane, chloroform, carbon tetrachloride, acetonitrile, nitromethane, ethyl acetate, benzene etc.

The amount of catalyst is variable according to the reactants. An amount of at least 1 molar amount is desirable in case said radical X is alkoxy, alkyloxycarbonyl or aryloxycarbonyl, but an amount of 0.1-0.2 molar amount is enough for the progress of reaction in case said radical X is a halogen atom. In general an elevated amount of catalyst provides a higher reaction speed but does not give direct effect on the yield of product.

The reaction temperature is dependent on the 2-substituted tetrahydrofurane to be employed in the reaction, and is lowered preferably to a range of $-5°$ C.$--40°$ C. in case of 2-halogenated tetrahydrofurans, particularly 2-chlorotetrahydrofurane, which are apt to decompose at ambient temperature.

The reaction temperature is subject to no specific limitation in case of other 2-substituted tetrahydrofurans, and can be suitably selected within a range from $-10°$ C. to $100°$ C. according to the desired product. However the preferred reaction temperature is within a range from $-5°$ C. to $30°$ C., more preferably within a range from $-5°$ C. to $10°$ C.

This reaction provides principally 1-substituted compound (compound I) in case of a short reaction time since the nitrogen atom in 1-position is at first activated by substitution of uracil derivative with alkylstannyl radical. Successively there is formed, in case of a reaction time over 3 hours, 3-substituted compound (compound II) which is presumably generated by migration of substituent in 1-position to 3-position, and the ratio of 1-substituted compound and 3-substituted compound is approximately 1:1 and remains unchanged in an equilibrium state even when the reaction time is prolonged to 20 hours.

Although the reaction time is influenced by the reaction temperature, the mono-substituted uracil obtained is variable according to the reaction time and is principally the compound I in case the reaction time is short, while it is a mixture of the compounds I and II in case the reaction time is extended.

Generally speaking this reaction provides mono-substituted compounds in case the molar ratio of uracil derivative and tetrahydrofurane derivative is within the range of 1:1.0-1.5 preferably 1:1.0-1.2, a di-substituted compound in case said ratio is 1:2 or higher, or a mixture of mono- and di-substituted compounds at a molar ratio therebetween, although the species and ratio of reaction products are variable to a certain extent depending on various factors such as reaction time, reaction temperature and amount of catalyst.

In the following there are shown preferred reaction conditions for each type of reaction product.

The $N_1$-monosubstituted compound (compound I) is obtainable in a reaction with a molar ratio within a range of 1:1.-1.5 preferably 1:1.0-1.2. In this case the reaction temperature and reaction time are not critical and variable in ranges respectively of $-50°$ C. to $100°$ C. and of 30 minutes to 3 hours, preferably, however within ranges of −5° to 10° C. and of 30 minutes to 2 hours.

For obtaining a mixture of $N_1$-mono-substituted compound (compound I) and $N_3$-mono-substituted compound (compound II), the reaction temperature and reaction time are variable with ranges respectively of −50° C. to 100° C. and of 3 to 20 hours, preferably, however, within ranges of 5° to 10° C. and of 5 to 10 hours. In this case the reaction time is naturally shortened at a higher reaction temperature.

The $N_1$-mono-substituted compound (compound I) and $N_3$-mono-substituted compound (compound II) can be respectively isolated from such mixture by means of a chromatographic method. Both compounds are endowed with pharmaceutical effects as explained before. Particularly $N_3$-mono-substituted compound is considered capable of exhibiting an anticancer effect similar to that of $N_1$-substituted compound.

Furthermore, the $N_1,N_3$-di-substituted compound (compound III) is obtainable in a reaction conducted at a molar ratio of bis(tri-lower alkyl stannyl)-5-fluorouracil to 2-substituted tetrahydrofurane equal to or higher than 1:2. The preferred range of said molar ratio is from 1:2 to 1:3, as the use of an overly excessive amount of 2-substituted tetrahydrofurane does not improve the yield of desired compound but merely results in a loss of 2-substituted tetrahydrofurane.

A reaction conducted with a molar ratio lower than 1:2 will lead to the formation of a mixture of said di-substituted compound (compound III) and said $N_1$-mono-substituted compound (compound I). With a further prolonged reaction time in this case there will be formed a mixture of $N_1,N_3$-di-substituted compound, $N_1$-mono-substituted compound and $N_3$-mono-substituted compound due to the transformation of $N_1$-monosubstituted compound (compound I) into $N_3$-mono-substituted compound (compound II).

The reaction in this case can be advantageously conducted at a reaction temperature and a reaction period within ranges respectively of −50° to 100° C. and of 30 minutes to 3 hours, most preferably of −5° to 10° C. and of 30 minutes to 1 hour. The reaction time is naturally shortened at a higher reaction temperature, and a prolonged reaction time, for example of 7 hours, will result in a lowered yield of the desired products.

The reaction according to the process of the present invention can be conducted in the following manner.

Preferably the uracil derivative and the tetrahydrofurane derivative are dissolved in a solvent, maintained at a determined temperature and reacted under agitation for a given period with the addition of a given amount of catalyst at one time or in divided portions.

After the completion of the reaction, the reaction mixture is poured over an ice-alkali solution mixture to decompose the catalyst or to transfer it into the aqueous phase. The aqueous phase is extracted with a solvent, and the extract is washed with water, combined with organic phase, dried and concentrated to obtain the reaction product which is then recrystallized.

In case of a reaction with a catalyst, such as boron trifluoride, decomposible with alcohols such as methanol, the reaction mixture is added with an alcohol to decompose the catalyst. After the elimination of solvent by distillation, the remaining residue is dissolved in a solvent such as chloroform, and the unreacted 5-halogenouracil undissolved therein is recovered by filtration. The chloroform solution is concentrated and added with hexane to precipitate the reaction product which can be collected by filtration, eventually followed by recrystallization for further purification. Also bis(tri-alkylstannyl)oxide can be recovered from the filtrate in the following manner.

Said filtrate is refluxed with alcoholic solution of alkali hydroxide, and the obtained reaction mixture, from which alcohol is eliminated by distillation is added with water to remove remaining alkali, and extracted with a polar solvent such as methylene chloride. The extract is evaporated dry to recover bis(tri-alkylstannyl)oxide.

The $N_1$-substituted compound or $N_1,N_3$-di-substituted compound can be obtained in isolated state by means of the above-mentioned processes.

In case the reaction provides a mixture of $N_1$-substituted compound and $N_3$-substituted compound or a mixture of di-substituted compound and mono-substituted compounds, each component can be isolated from such mixtures by means of a chromatographic procress or a fractional crystallization.

Furthermore, the present inventors have found that the $N_1,N_3$-di-substituted compound can be converted, through acidolysis thereof to selectively cleave the substituent on the nitrogen atom in 3-position, into $N_1$-mono-substituted compound. For this purpose the $N_1,N_3$-di-substituted compound resulting from the above-mentioned reaction is stirred for a short period with a Lewis acid or an inorganic acid, and the reaction mixture is poured in a mixture of ice and alkali solution to separate the organic phase. The aqueous phase is extracted with an organic solvent, and the extract, united with the organic phase, is dried, then concentrated under a reduced pressure and subjected to a chromatographic separation to obtain the $N_1$-mono-substituted compound with a high yield.

The hydrolysis mentioned above can be advantageously conducted with hydrochloric acid, acetic acid or a Lewis acid of a concentration of 0.01 to 10% and with an agitation for 1 minute to 24 hours at room temperature.

The present invention will be further clarified by the following examples, which are solely shown for the purpose of illustration and by no means limit the scope of the present invention.

EXAMPLE 1

1.30 gr. (0.01 mol) of 5-fluorouracil and 5.96 gr. (0.01 mol) of bis(tri-n-butylstannyl)oxide were heated under reflux in 100 ml of toluene, while water formed was continuously distilled off during the heating. After heating for ca. 20 hrs., toluene was removed by distillation to obtain bis(tri-n-butylstannyl)-5-fluorouracil.

Physical property

Nuclear magnetic resonance spectrum ($^1$H, N.M.R.): (CDCl$_3$) $\delta$H$_6$, 7.10 (d, j=5 Hz)

EXAMPLE 2

The process of Example 1 was repeated with 1.91 gr. (0.01 mol) of 5-bromouracil to obtain bis(tri-n-butylstannyl)-5-bromouracil.

EXAMPLE 3

The process of Example 1 was repeated with 51.8 gr. (0.1 mol) of bis(tri-n-propylstannyl)oxide instead of bis(tri-n-butylstannyl)oxide to obtain bis(tri-n-propylstannyl)-5-fluorouracil.

EXAMPLE 4

0.192 gr. (1 mmol) of 2-benzoxytetrahydrofrane and 0.708 gr. (1 mmol) of bis(tri-n-butylstannyl)-5-fluorouracil obtained in the Example 1 were dissolved in 10 ml of dichloromethane, cooled at −5°-0° C., added with 0.26 gr. (1 mmol) of stannic chloride under agitation and maintained at 0°-5° C. After 30 to 60 minutes the reaction mixture was poured over a mixture of ice and sodium bicarbonate solution, and extracted with dichloromethane. The extract was washed with water, then dried over anhydrous magnesium sulfate, concentrated under a reduced pressure and passed through a silica gel column. The resulting product was recrystallized from ethanol to obtain 0.140 gr. (yield 70%) of $N_1$-(2'-tetrahydrofuranyl)-5-fluorouracil.

Physical properties

Melting point: 165°-167° C.
N.M.R. spectrum:
  $\delta 6.0$ ppm, 1H
  broad doublet J=6 Hz

EXAMPLE 5

The process of Example 4 was repeated with bis(tri-n-butylstannyl)-5-bromouracil to obtain 0.177 gr. (yield 69%) of $N_1$-tetrahydrofuranyl-5-bromouracil.

EXAMPLE 6

The process of Example 4 was repeated with 6.24 gr. (0.01 mol) of bis(tri-n-propylstannyl)-5-fluorouracil instead of bis(tri-n-butylstannyl)-5-fluorouracil to obtain 1.54 gr. (yield 77.0%) of $N_1$-(2'-tetrahydrofuranyl)-5-fluorouracil.

EXAMPLE 7

17.7 gr. (0.025 mol) of bis(tri-n-butylstannyl)-5-fluorouracil obtained in the Example 1 and 7.2 gr. (0.0375 mol) of 2-benzoyloxytetrahydrofurane were dissolved in 100 ml of dichloroethane. 2.48 gr. (0.0175 mol) of boron trifluoride etherate dissolved in 30 ml of dichloroethane was added dropwise from a dropping funnel over a period of 30 minutes to the above-obtained solution maintained at 15° C., and the resulting mixture was allowed to stand for 30 minutes to complete the reaction. After the completion of reaction, 30 ml of methanol was added and the solvent was eliminated by distillation. The resulting residue was dissolved in chloroform to recover undissolved 5-fluorouracil, and the chloroform solution was again concentrated and added with hexane. The resulting crystals were separated by filtration to obtain 4.2 gr. of $N_1$-(2'-tetrahydrofuranyl)-5-fluorouracil (yield 95%: m.p. 165°-167° C.). Also 0.35 gr. of 5-fluorouracil was recovered in the process.

EXAMPLE 8

The process of Example 4 was repeated with the reaction time extended to 7 hours to obtain 1-(tetrahydrofuranyl)-5-fluorouracil and $N_3$-(2'-tetrahydrofuranyl)-5-fluorouracil in 1:1 molar ratio. Said reaction products were isolated respectively in amount of 0.06 gr. (yield 30%) and 0.05 gr. (yield 25%) through the procedure and chromatographic separation described in the Example 4.

Physical properties of $N_3$-(2'-tetrahydrofuranyl)-5-fluorouracil

Melting point: 125°-127° C.
N.M.R. spectrum:
  $\delta 5.85$
  1H doublet

EXAMPLE 9

The filtrate obtained after separation of 4.2 gr. of crystals in the Example 7 was concentrated, and refluxed for ca. 5 hrs. with 4 gr. of sodium hydroxide and 150 ml of methanol. After elimination of methanol by distillation, the reaction mixture was added with water and extracted with methylene chloride. The methylene chloride was distilled off to obtain an oily residue, from which a fraction distilling between 150° and 158° C. was collected to recover bis(tri-n-butylstannyl)oxide. The yield of recovery was 80%.

EXAMPLE 10

1.30 gr. (0.01 mol) of 2-acetoxytetrahydrofurane and 7.08 gr. (0.01 mol) of bis(tri-n-butylstannyl)-5-fluorouracil obtained in the Example 4 were dissolved in 100 ml of dichloromethane, cooled to −5° C. and added with 2.6 gr. (0.01 mol) of stannic chloride under agitation. After the completion of reaction (ca. 3 hrs.), the reaction mixture was poured over a mixture of ice and sodium bicarbonate solution, and extracted with dichloromethane. The extract was washed with water, then dried over anhydrous magnesium sulfate and concentrated under a reduced pressure. After passing a silica gel column, the obtained product was recrystallized from ethanol to obtain 1.5 gr. of $N_1$-(2'-tetrahydrofuranyl)-5-fluorouracil (yield 75%: m.p. 165°-167° C.).

EXAMPLE 11

1.06 gr. (0.01 mol) of 2-chlorotetrahydrofurane and 7.08 gr. (0.01 mol) of bis(tri-n-butylstannyl)-5-fluorouracil were dissolved in 100 ml. of dichloromethane and agitated at −5° C. for ca. 3 hrs. After the completion of reaction, the reaction mixture was poured over a mixture of ice and sodium bicarbonate solution, and extracted with dichloromethane. The extract was washed with water, dried over anhydrous magnesium sulfate and evaporated dry under a reduced pressure. After passing a silica gel column, the obtained product was recrystallized from ethanol to obtain 1.66 gr. of $N_1$-(2'-tetrahydrofuranyl)-5-fouorouracil (yield 83%: m.p. 165°-167° C.).

EXAMPLE 12

1.02 gr. (0.01 mol) of 2-methoxytetrahydrofurane and 7.08 gr. (0.01 mol) of bis(tri-n-butylstannyl)-5-fluorouracil were dissolved in 100 ml of dichloromethane, and added at 10° C. and under agitation, with 2.6 gr. (0.01 mol) of stannic chloride. After completion of reaction for ca. 2 hrs, the reaction mixture was poured over a mixture of ice and sodium bicarbonate solution, and extracted with dichloromethane. The extract was washed with water, then dried over anhydrous magnesium sulfate and concentrated under a reduced pressure. After passing a silica gel column and concentration under a reduced pressure, the reaction product was recrystallized from ethanol to obtain 1.6 gr. of $N_1$-(2'-tetrahydrofuranyl)-5-fluorouracil (yield 80.0%: m.p. 165°-167° C.).

EXAMPLE 13

0.114 gr. (1 mmol) of 2-ethoxytetrahydrofurane and 0.708 gr. (1 mmol) of bis(tri-n-butylstannyl)-5-fluorouracil obtained in the Example 1 were dissolved in 10 ml of dichloromethane, cooled to −5° to 0° C., then added under agitation with 2.6 gr. (1 mmol) of stannic chloride and maintained at 0°–5° C. After reaction for 30 to 60 minutes, the reaction mixture was poured over a mixture of ice and sodium bicarbonate solution and extracted with dichloromethane. The extract was washed with water, dried over anhydrous magnesium sulfate and concentrated under a reduced pressure. After passing a silica gel column, the obtained product was recrystallized from ethanol to obtain 1.40 gr. of 1-(tetrahydrofuranyl)-5-fluorouracil (yield 70%).

EXAMPLE 14

The process of Example 4 was repeated with 0.2 ml of boron trifluoride etherate instead of stannic chloride to obtain 1.4 gr. of $N_1$-(2'-tetrahydrofuranyl)-5-fluorouracil (yield 70%).

EXAMPLE 15

The process of Example 4 was repeated with reaction time prolonged to 7 hours to obtain $N_1$-(tetrahydrofuranyl)-5-fluorouracil and $N_3$-(tetrahydrofuranyl)-5-fluorouracil in 1:1 molar ratio. The products were treated as described in the Example 4, then dissolved in toluene-ethyl acetate (1:1) mixture and subjected to chromatographic separation, which eluded at first 0.060 gr. (yield 30%) of $N_1$-substituted compound and then 0.050 gr. (yield 25%) of $N_3$-substituted compound.

EXAMPLE 16

The process of Example 15 was repeated with 0.13 gr. (1 mmol) of 2-acetoxytetrahydrofurane to obtain 0.058 gr. (yield 29%) of $N_1$-(tetrahydrofuranyl)-5-fluorouracil and 0.052 gr. (yield 26.0%) of $N_3$-(tegrahydrofuranyl)-5-fluorouracil.

EXAMPLE 17

The process of Example 15 was repeated with 0.10 gr. (1 mmol) of 2-methoxytetrahydrofurane to obtain 0.060 gr. (yield 30.0%) of $N_1$-(tetrahydrofuranyl)-5-fluorouracil and 0.052 gr. (yield 26.0%) of $N_3$-(tetrahydrofuranyl)-5-fluorouracil.

EXAMPLE 18

The process of Example 15 was repeated with 0.11 gr. (1 mmol) of 2-chlorotetrahydrofuran and without stannic chloride to obtain 0.064 gr. (yield 32.0%) of $N_1$-(tetrahydrofuranyl)-5-fluorouracil and 0.048 gr. (yield 24.0%) of $N_3$-(tetrahydrofuranyl)-5-fluorouracil.

EXAMPLE 19

The process of Example 15 was repeated with 0.24 gr. (1 mmol) of 2-(p-nitrobenzoyl)tetrahydrofurane to obtain 0.05 gr. (yield 29.5%) of $N_1$-(tetrahydrofuranyl)-5-fluorouracil and 0.052 gr. (yield 26.0%) of $N_3$-(tetrahydrofuranyl)-5-fluorouracil.

EXAMPLE 20

The process of Example 15 was repeated with 0.22 gr. (1 mmol) of 2-(p-tolylbenzoxy)-tetrahydrofurane to obtain 0.058 gr. (yield 29.0%) of $N_1$-(tetrahydrofuranyl)-5-fluorouracil and 0.050 gr. (yield 25.0%) of $N_3$-(tetrahydrofuranyl)-5-fluorouracil.

EXAMPLE 21

The process of Example 18 was repeated with 0.09 gr. (1 mmol) of 2-chlorotetrahydrofurane to obtain 0.062 gr. (yield 31.0%) of $N_1$-(tetrahydrofuranyl)-5-fluorouracil and 0.051 gr. (yield 25.5%) of $N_3$-(tetrahydrofuranyl)-5-fluorouracil.

EXAMPLE 22

The process of Example 15 was repeated but with a reaction time of 4 hours and with a reaction temperature of 20° C. to obtain 0.066 gr. (yield 33%) of $N_1$-(tetrahydrofuranyl)-5-fluorouracil and 0.046 gr. (yield 23%) of $N_3$-(tetrahydrofuranyl)-5-fluorouracil.

EXAMPLE 23

The process of Example 16 was repeated but with a reaction time of 4 hours and a reaction temperature of 20° C. to obtain 0.064 gr. (yield 32%) of $N_1$-(tetrahydrofuranyl)-5-fluorouracil and 0.046 gr. (yield 23%) of $N_3$-(tetrahydrofuranyl)-5-fluorouracil.

EXAMPLE 24

The process of Example 18 was repeated but with a reaction time prolonged to 7 hours to obtain 0.077 gr. (yield 30%) of $N_1$-(tetrahydrofuranyl)-5-bromouracil and 0.062 gr. (yield 24%) of $N_3$-(tetrahydrofuranyl)-5-bromouracil.

EXAMPLE 25

The process of Example 24 was repeated but with 0.13 gr. (1 mmol) of 2-acetoxytetrahydrofurane to obtain 0.075 gr. (yield 29%) of $N_1$-(tetrahydrofuranyl)-5-bromouracil and 0.064 gr. (yield 25%) of $N_3$-(tetrahydrofuranyl)-5-bromouracil.

EXAMPLE 26

9.6 gr. (0.05 mol) of 2-benzoxytetrahydrofurane and 17.7 gr. (0.025 mol) of bis(tri-n-butylstannyl)-5-fluorouracil obtained in the Example 1 were dissolved in 100 ml of dichloroethane, then added, at −5° to 0° C. and under agitation, with 13 gr. (0.05 mol) of stannic chloride and maintained at 0° to 5° C.

After 30 minutes, the reaction mixture was poured over a mixture of ice and sodium bicarbonate solution and extracted with chloroform. The extract was dried over anhydrous magnesium sulfate, concentrated under a reduced pressure and passed through a silica gel column to obtain 6.2 gr. (yield 91.8%) of N,N'-bis-(2'-tetrahydrofuranyl)-5-fluorouracil as an oily substance.

Physical properties

N.M.R. spectrum:
  $\delta 6.64$ 1H
  J=6 Hz
  $\delta 5.95$, 1H
  J=6 Hz

EXAMPLE 27

The process of Example 26 was repeated but with 6.5 gr. (0.05 mol) of 2-acetoxytetrahydrofurane to obtain 6.0 gr. (yield 88.0%) of N,N'-bis-(2'-tetrahydrofuranyl)-5-fluorouracil.

EXAMPLE 28

5.5 gr. (0.05 mol) of 2-chlorotetrahydrofurane was dissolved in 100 ml of dichlorethane, to which 17.7 gr. (0.025 mol) of bis(tri-n-butylstannyl)-5-fluorouracil obtained in the Example 1 was added at −10° to 0° C. and under agitation. After 1 hour, the reaction mixture was poured over a mixture of ice and sodium bicarbonate solution, and extracted with chloroform. The extract was treated as described in the Example 26 to obtain 6.1 gr. (yield 90.3%) of N,N'-bis-(2'-tetrahydrofuranyl)-5-fluorouracil.

EXAMPLE 29

The process of Example 26 was repeated but with 5.3 gr. (0.05 mol) of 2-methoxytetrahydrofurane to obtain 6.0 gr. (yield 88.0%) of N,N'-bis-(2'-tetrahydrofuranyl)-5-fluorouracil.

EXAMPLE 30

The process of Example 26 was repeated but with 9.6 gr. (0.05 mol) of 2-benzoxytetrahydrofurane and 14.2 gr. (0.02 mol) of bis(tri-n-butylstannyl)-5-fluorouracil to obtain 5.1 gr. (yield 95.0%) of N,N'-bis-(2'-tetrahydrofuranyl)-5-fluorouracil.

EXAMPLE 31

The process of Example 26 was repeated but with 10.5 gr. (0.06 mol) of 2-benzoxytetrahydrofurane and 14.2 gr. (0.02 mol) of bis(tri-n-butylstannyl)-5-fluorouracil to obtain 5.0 gr. (yield 93.5%) of N,N'-bis-(2'-tetrahydrofuranyl)-5-fluorouracil.

EXAMPLE 32

The process of Example 26 was repeated but with a reaction time of 3 hours to obtain 5.6 gr. (yield 83.0%) of N,N'-bis-(2'-tetrahydrofuranyl)-5-fluorouracil.

EXAMPLE 33

The process of Example 26 was repeated but with a reaction time of 7 hours to obtain 5.1 gr. (yield 75.0%) of N,N'-bis(2'-tetrahydrofuranyl)-5-fluorouracil.

EXAMPLE 34

The process of Example 26 was repeated but with 15.8 gr. (0.025 mol) of bis(tri-n-propylstannyl)-5-fluorouracil to obtain 6.1 gr. (yield 90.3%) of N,N'-bis-(2'-tetrahydrofuranyl)-5-fluorouracil.

EXAMPLE 35

The process of Example 26 was repeated but with 10.5 gr. (0.06 mol) of 2-benzoxytetrahydrofurane and 23.5 gr. (0.04 mol) of bis(tri-n-butylstannyl)-5-fluorouracil to obtain 5.1 gr. (yield 47.0%) of N,N'-bis-(2'-tetrahydrofuranyl)-5-fluorouracil and 1.2 gr. (yield 14.5%) of $N_1$-(2'-tetrahydrofuranyl)-5-fluorouracil.

EXAMPLE 36

6.75 gr. (0.025 mol) of N,N'-bis-(2'-tetrahydrofuranyl)-5-fluorouracil was dissolved in 50 ml of methanol, and 2.48 gr. of boron trifluoride etherate at room temperature. After agitation for ca. 1 hour, the reaction mixture was poured over a mixture of ice and sodium bicarbonate solution and extracted with chloroform. The extract was dried over anhydrous magnesium sulfate and concentrated under a reduced pressure. After passing a silica gel column, the obtained product was recrystallized from ethanol to obtain 4.5 gr. (yield 90%) of $N_1$-(tetrahydrofuranyl)-5-fluorouracil.

EXAMPLE 37

6.75 gr. (0.025 mol) of N,N'-bis-(2'-tetrahydrofuranyl)-5-fluorouracil) was dissolved in 50 ml. of 1% methanolic solution of hydrochloric acid, then refluxed for ca. 10 minutes. and cooled. After neutralization of hydrochloric acid, the reaction mixture was subjected to extraction, drying and recrystallization as described in the Example 36 to obtain 4.0 gr. (yield 80%) of $N_1$-(tetrahydrofuranyl)-5-fluorouracil.

EXAMPLE 38

9.6 gr. (0.05 mol) of 2-benzoxytetrahydrofurane and 17.7 gr. (0.025 mol) of bis(tri-n-butylstannyl)-5-fluorouracil obtained in the Example 1 were dissolved in 100 ml of dichlorethane, then added, at −5° to 0° C. and under agitation, with 13 gr. (0.05 mol) of stannic chloride and maintained at 0° to 5° C.

After 30 minutes the reaction mixture was poured over a mixture of ice and sodium bicarbonate solution and extracted with chloroform. The extract was dried over anhydrous magnesium sulfate and concentrated under a reduced pressure. The resulting oily substance was dissolved in 50 ml of methanol, then added with 2.48 gr. of boron trifluoride etherate at room temperature and stirred for ca. 1 hour. Successively the reaction mixture was poured over a mixture of ice and sodium bicarbonate solution and extracted with chloroform. The extract was dried over anhydrous magnesium sulfate and concentrated under a reduced pressure. After passing a silica gel column, the obtained product was recrystallized from ethanol to obtain 4.5 gr. (yield 90%) of $N_1$-(2'-tetrahydrofuranyl)-5-fluorouracil.

The above-mentioned oily substance was purified and identified as N,N'-bis-(2'-tetrahydrofuranyl)-5-fluorouracil.

Physical properties

N.M.R. spectrum:
 δ6.64, 1H
 J=6 Hz
 δ5.95, 1H
 J=6 Hz

EXAMPLE 39

6.5 gr. (0.05 mol) of 2-acetoxytetrahydrofurane and 17.7 gr. (0.025 mol) of bis(tri-n-butylstannyl)-5-fluorouracil were dissolved, then added with 13 gr. (0.05 mol) of stannic chloride at −5° to 0° C. and under agitation, and maintained at 0° to 5° C.

After 1 hour, the reaction mixture was poured over a mixture of ice and sodium bicarbonate solution and extracted with chloroform. The extract was dried over anhydrous magnesium sulfate and concentrated under a reduced pressure. The resulting oily substance was dissolved in 50 ml of 1% methanolic solution of hydrochloric acid, refluxed for ca. 10 minutes, and cooled. After neutralization of hydrochloric acid, the reaction mixture was subjected to extraction, drying and recrystallization as described in the Example 7 to obtain 4.4 gr. (yield 88.0%) of $N_1$-(2'-tetrahydrofuranyl)-5-fluorouracil.

EXAMPLE 40

5.5 gr. (0.05 mol) of 2-chlorotetrahydrofurane was dissolved in 100 ml of dichlorethane, to which 17.7 gr. (0.025 mol) of bis(tri-n-butylstannyl)-5-fluorouracil obtained by the Example 1 was added at −10° to 0° C. and under agitation. After 1 hour the reaction mixture was poured over a mixture of ice and sodium bicarbonate solution and extracted with chloroform. The extract was treated as described in the Example 38 to obtain 4.6 gr. (yield 92.0%) of N₁-(tetrahydrofuranyl)-5-fluorouracil.

EXAMPLE 41

The process of Example 39 was repeated but with 5.3 gr. (0.05 mol) of 2-methoxytetrahydrofurane to obtain 4.4 gr. (yield 88.0%) of N₁-(2'-tetrahydrofuranyl)-5-fluorouracil.

EXAMPLE 42

The process of Example 39 was repeated but with 9.6 gr. (0.05 mol) of 2-benzoxytetrahydrofurane and 14.2 gr. (0.02 mol) of bis(tri-n-butylstannyl)-5-fluorouracil to obtain 3.8 gr. (yield 95.0%) of N₁-(2'-tetrahydrofuranyl)-5-fluorouracil.

EXAMPLE 43

The process of Example 39 was repeated but with 10.5 gr. (0.06 mol) of 2-benzoxytetrahydrofurane and 14.2 gr. (0.02 mol) of bis(tri-n-butylstannyl)-5-fluorouracil to obtain 3.7 gr. (yield 92.5%) of N₁-(2'-tetrahydrofuranyl)-5-fluorouracil.

EXAMPLE 44

The process of Example 38 was repeated but with a reaction time of 3 hours to obtain 4.2 gr. (yield 83.0%) of N₁-(2'-tetrahydrofuranyl)-5-fluorouracil.

EXAMPLE 45

The process of Example 38 was repeated but with a reaction time of 7 hours to obtain 3.8 gr. (yield 76.0%) of N₁-(2'-tetrahydrofuranyl)-5-fluorouracil.

EXAMPLE 46

The process of Example 38 was repeated but with 15.8 gr. (0.025 mol) of bis(tri-n-propylstannyl)-5-fluorouracil obtained in Example 3 to obtain 4.5 gr. (yield 90.0%) of N₁-(2'-tetrahydrofuranyl)-5-fluorouracil.

EXAMPLE 47

1.30 gr. (0.01 mol) of 5-fluorouracil and 5.96 gr. (0.01 mol) of bis(tri-n-butylstannyl)oxide were heated under reflux in 100 ml of toluene while water was continuously eliminated by distillation. After about 20 hours toluene was distilled off to obtain crude bis(tri-n-butylstannyl)-5-fluorouracil.

Physical properties

N.M.R. spectrum ('H NMR): (CDCl₃) δH₆ 7.10 (d, J=5 Hz)

EXAMPLE 48

11.2 gr. (0.1 mol) of 2,4-dihydroxypyrimidine and 59.4 gr. (0.1 mol) of bis(tri-n-butylstannyl)oxide were refluxed in toluene with continuous elimination of formed water. After the completion of reaction the reaction mixture was concentrated to obtain 2,4-bis(tri-n-butylstannyl)pyrimidine in an approximately quantitative yield.

Physical property

Mass spectrum: M⁺ = 690

EXAMPLE 49

The process of Example 1 was repeated with 12.7 gr. (0.1 mol) of 2-hydroxy-5-methyl-5-hydroxypyrimidine to obtain 2,4-bis(tri-n-butylstannyl)-5-methylpyrimidine in an approximately quantitative yield.

Physical property

N.M.R. spectrum ('H N.M.R.):
δ6.87 (1H, S; H-6)
δ1.88 (3H, S; C₅ -CH₃)

EXAMPLE 50

The process of Example 47 was repeated with 19.1 gr. (0.1 mol) of 2-hydroxy-5-bromo-4-hydroxypyrimidine to obtain 2,4-bis(tri-n-butylstannyl)-5-bromopyrimidine in an approximately quantitative yield.

Physical property

N.M.R. spectrum ('H N.M.R.): δ7.30 (1H, S; H-6)

EXAMPLE 51

The process of Example 47 was repeated with 12.8 gr. (0.1 mol) of 2-thio-4-hydroxyprimidine to obtain 2-thio(tri-n-butylstannyl)-4-tri-n-butylstannylpyrimidine in an approximately quantitative yield.

Physical property

δ6.17 (1H, d, J=6 Hz; H-5)
δ7.80 (1H, d, J=6 Hz; H-6)

What we claim is:

1. A di(tri-lower alkylstannyl)pyrimidine derivative having the general formula:

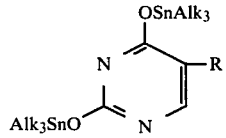

wherein Alk stands for a lower alkyl radical and R for a hydrogen or fluorine or bromine atom or a lower alkyl radical.

2. A process for producing di(tri-lower alkylstannyl) primidine derivatives having the general formula:

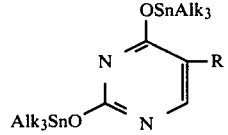

wherein Alk stands for a lower alkyl radical and R for a hydrogen or fluorine or bromine atom or a lower alkyl radical which comprises reacting 5-substituted uracil having the general formula:

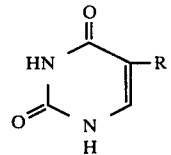

wherein R has the same meaning as above, under reflux with bis(tri-lower alkylstannyl)oxide having the formula;

(Alk₃Sn)₂O wherein Alk has the same meaning as the above, in the presence of an aprotic solvent with continuous elimination of water formed during the reaction.

* * * * *